US005665546A

United States Patent [19]
Cubbage et al.

[11] Patent Number: 5,665,546
[45] Date of Patent: Sep. 9, 1997

[54] FREE RADICAL SCAVENGERS USEFUL FOR REDUCING AUTOFLOURESCENCE IN FIXED CELLS

[75] Inventors: Michael Lee Cubbage; Shyh-Chen Ju, both of Houston; Joel Bresser, Bellaire; Rebecca Jurtshuk, Houston, all of Tex.

[73] Assignee: Aprogenex, Inc., Houston, Tex.

[21] Appl. No.: 393,945

[22] Filed: Feb. 22, 1995

Related U.S. Application Data

[63] Continuation of Ser. No. 915,893, Jul. 17, 1992, abandoned.
[51] Int. Cl.$^6$ .............................. C12Q 1/68; C12Q 1/70; C07H 21/02; G01N 33/567
[52] U.S. Cl. .................... 435/6; 536/26.6; 435/5; 435/7.21
[58] Field of Search ...................... 435/5, 6, 7.21; 935/77, 78; 536/23.1, 26.6

[56] References Cited

PUBLICATIONS

Poot, et al., Autofluorescence of Human Skin Fibroblasts During Growth Inhibition and in vitro Ageing, Gerontology, v. 31, pp. 158–165 (1985).

Deamer, et al., Autofluorescent Structures in Cultured WI–38 Cells, Archives of Biochemistry and Biophysics, v. 165, pp. 421–426 (1974).

Rattan, et al., Autofluorescence as an Index of Ageing in Human Fibroblasts in Culture, Bioscience Reports, v. 2, pp. 561–567 (1982).

McKenna, et al., Kinetic Analysis of the Free–Radical–Induced Lipid Peroxidation in Human Erythrocyte Membranes Evaluation of Potential Antioxidants Using CIS, Analytical Biochemistry, v. 196, pp. 443–450 (1991).

Kan, et al., Effect of Vitamin E on the Accumulation of Fluorescent Material in Cultured Cerebral Cortical Cells of Mice, Experimental Gerontology, v. 26, pp. 365–374 (1991).

Trask, Trends in Genetics 7(5): 149–154 (1991) "Fluorescence In Situ Hybridization".

*Primary Examiner*—Eggerton A. Campbell
*Attorney, Agent, or Firm*—Elman & Associates

[57] ABSTRACT

Assays for target molecules in cells and viruses whereby the use of free radical scavengers leads to decreased autofluorescence.

40 Claims, 2 Drawing Sheets

Fig. 2

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:

```
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( x i ) SEQUENCE DESCRIPTION: SEQ ID NO:1:

ATCAGAGTAG TGGTATTTCA CCGGC                                         25

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: N ( x i ) SEQUENCE DESCRIPTION: SEQ ID NO:2:

TACGCTCGAT CCAGCTATCA GCCGT                                         25
```

FREE RADICAL SCAVENGERS USEFUL FOR REDUCING AUTOFLOURESCENCE IN FIXED CELLS

This application is a Continuation of U.S. patent application Ser. No. 07/915893, filed on Jul. 17, 1992, abandoned.

FIELD OF THE INVENTION

The invention pertains to the reduction of background autofluorescence in fluorimetrically-monitored assays for specific molecules in cells and viruses.

BACKGROUND OF THE INVENTION

In an important type of in situ assay, a cell (or virus) is incubated with a target-specific probe that is either a fluorescent dye or a fluorescent dye attached to a target-specific molecule. Detection is normally accomplished with a flow cytometer or microscope. Such assays are useful to detect viral nucleic acids, human genes of interest, specific cellular antigens, and other biologically important molecules.

In the first steps of a fluorimetric measurement, a cell is exposed to light with a wavelength that the probe dye can absorb. The dye will then emit light at a longer wavelength. A significant problem, however, is that the light emitted by a probe-treated cell will not exclusively originate from fluorescent probe molecules bound to specific target molecules. Rather, some of the light emitted will be from cellular molecules that are not bound to probe molecules. Additionally, some light will be emitted from probe molecules that have bound non-specifically.

Light emitted by cellular molecules (or vital molecules) not bound to probe molecules is referred to as autofluorescence, and such light-emitting molecules are autofluorescing molecules. Autofluorescence occurs at wavelengths in the range 470 nm to 570 nm, as well as above and below that range; a major peak in the spectrum is at about 520 nm. If the emission wavelengths of the probe dye are also in the range 470 nm to 570 nm, then autofluorescence will contribute significantly to the assay background. An example of a commonly used probe dye that emits in that range is fluorescein isothiocyanate ("FITC"). Autofluorescence can, however, also be important when other probe dyes, such as phycoerythrin, are used.

The present invention involves the discovery of compounds useful as background reducers in in situ assays.

In addition to the general benefit of increased assay sensitivity that the background reducers provide, there is the additional advantage that, for a given level of sensitivity to be reached, cell treatment procedures such as cell fixation need not be as detrimental to cell integrity as would be the case without the use of the background reducers. As a result, the cells retain their structural integrity for a longer time, a consideration particularly important for flow cytometry.

BRIEF SUMMARY OF THE INVENTION

The invention is, in part, in situ assays in which free radical scavengers are added in order to reduce autofluorescence.

The solutions that contain the free radical scavengers are also inventions.

THE PRIOR ART

M. Poot et al. GERONTOLOGY, 31, 158–165 (1985) reported that Vitamin E, a lipophilic radical scavenger, decreased auto fluorescence in human skin fibroblasts.

D. W. Deamer and J. Gonzales, Archives of Biochemistry and Biophysics, 165, 421–426 (1974), used autofluorescence as an indicator of cell aging and cited K. S. Chio and A. L. Tappel, Biochemistry 8, 2821 (1969) and K. S. Chio et al, Science, 166, 1535 (1969) as disclosing that peroxidative damage leads to fluorescent products, especially flavins (fluorescence peak at about 520 nm) and aminoiminopropane compounds (fluorescence peak at about 470 nm).

S. I. Rattan et al, Bioscience Reports, 2, 561–567 (1982), used autoflourescence as an index of aging and suggested that peroxidative damage leads to age pigments that fluoresce when excited with ultra-violet light.

BRIEF DESCRIPTION OF THE DRAWINGS

FIG. 2. "Count vs. LFL1" histograms, generated by including vitamin E in the cocktail (based on our histogram #2523)

DETAILED DESCRIPTION

Figure 1:
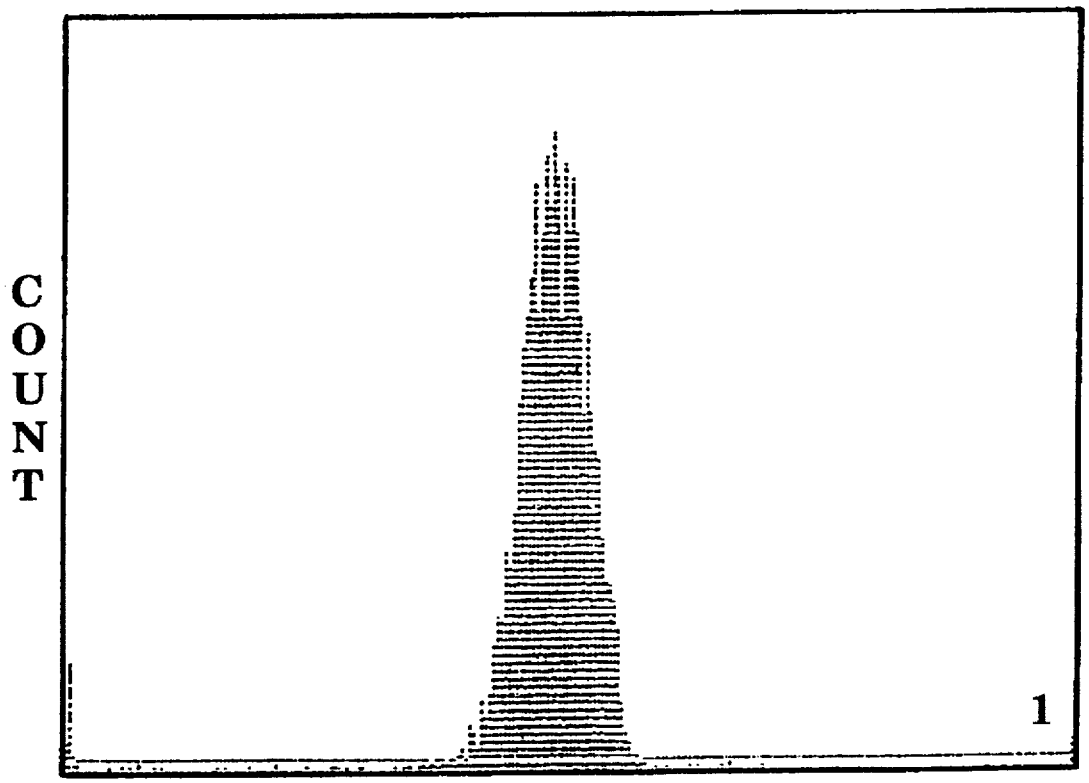
FIG. 1. "Count vs. LFL1" histograms, generated in the absence of free radical scavengers. (based on our histogram #2522)

In a general aspect, the invention is a fluorimetric detection process or assay capable of detecting a target molecule in or on a biological entity (cell or virus). The process comprises the steps of:

(1) contacting the biological entity with a solution comprising a fluorescent probe capable of binding to a target molecule in or on said biological entity, said contacting performed in a manner such that the fluorescent probe binds to said target molecule so as to make that probe a biological entity-bound probe, (2) contacting the biological entity with a solution comprising a free radical scavenger, (3) causing the biological entity-bound probe to absorb light of wavelengths that are fluorescent absorption wavelengths of said biological entity-bound probe, and (4) detecting light of a wavelengths that are fluorescent emission wavelengths of said biological entity-bound probe;

wherein step (1) takes place before step (2), after step (2), or during step (2).

Steps (1) and (2) are considered to take place simultaneously if the fluorescent probe and the free radical scavenger are in the same solution.

Preferably steps (1) and (2) are performed simultaneously by including the fluorescent probe and the free radical scavenger in the same solution.

It is preferred that the free radical scavenger be chosen to meet the condition that, during step (4) of the process, the amount of light emitted by the scavenger does not exceed the scavenger-caused decrease in auto fluorescence. Whether a scavenger meets that condition for a given combination of fluorescent absorption and fluorescent emission wavelengths can be determined by performing the process twice, once without the scavenger and once with the scavenger (in both cases, the probe may be omitted from the process).

Free radical scavengers include compounds the following four classes:

1) Compounds that are hydrogen donors. Preferred hydrogen donors are compounds with thiol groups, especially those linked to aromatic groups.

2) Compounds which are not hydrogen donors but which have a free radical that is capable of combining with other free radicals. Examples are the N-hydroxy derivatives such as the dye Tempo, hydrazine derivatives such as DIPH, and azo derivatives in which a nitrogen, linked by a double bond to another nitrogen and by a single bond to a carbon atom, carries the free radical. Optimally these compounds have a structure so that stearic hindrance prevents them from reacting with each other instead of the free radical that has to be scavenged.

3) Parahydroxyaromatic compounds. Vitamin E is a compound in this class.

4) Compounds with unsaturated carbon atoms that quench radicals.

Many free radical scavengers, including ones that belong to the above groups have been identified by others.

A free radical scavenger can be defined by its ability to act as a free radical scavenger under defined conditions. If FRS stands for the compound to be tested as a free radical scavenger, then the following three-step assay can be used to confirm that FRS is a free radical scavenger:

1) FRS and 10 mg trichoroacetyl peroxide are mixed in 5 ml dimethylformamide such that the molar ratio of FRS to trichoroacetyl peroxide is 2:1.

2) The reaction mixture is heated to 80° C. for M minutes.

3) The reaction mixture is run on HPLC (if $Cl_3C$-FSR is not volatile) or on gas chromatography (if $Cl_3C$-FSR is volatile) and the amounts of $Cl_3C$-FRS is determined. The scavenging activity is defines as the amount of $Cl_3C$-FRS detected.

The time, M minutes, is chosen so that if Vitamin E is tested in the assay, the percentage of Vitamin E that is converted to $Cl_3C$-Vitamin E is less than 100. Generally, M is expected to be less than 10 minutes.

The relative scavenging activities of two compounds, (e.g., Vitamin E and another compound), can be calculated by comparing the amounts of $Cl_3C$-FRS formed when the two compounds are tested in the assay under identical conditions. If the amount of $Cl_3C$-FRS formed with a compound is 20 percent of that formed when vitamin E is added to the assay, then the scavenging activity of the compound is 20 percent of that of vitamin E.

The assay for measuring scavenging activity is based on a series of reactions wherein the treatment at 80° C. causes breakdown of one molecule of trichloroacetyl peroxide to produce two molecules of the free radical, $Cl_3C^*$, which then reacts with the free radical scavenger to produce $Cl_3C$-FRS.

A fluorescent absorption wavelength of a probe or compound (such as a free radical scavenger) is a wavelength of radiation (especially ultraviolet or visible light) that can be absorbed by the probe or compound and, if absorbed, can result in subsequent emission of radiation (especially visible light) by that probe or compound at a wavelength longer than the fluorescent absorption wavelength. The aforementioned longer wavelength is referred to as a "fluorescent emission wavelength." A fluorescent absorption wavelength is preferably in the range of about 420 nm to 460 nm. The fluorescent emission wavelength is preferably in the range of about 450 nm to 690 nm. In practice, the probe population is exposed to a range of absorption wavelengths and the emitted light is monitored at a range of emission wavelengths.

A fluorescent probe or compound is one that has fluorescent absorption wavelengths and fluorescent emission wavelengths.

In the fluorimetric detection process of this invention, free radical scavengers that have a free radical scavenging activity at least 1% of that of Vitamin E are preferred (scavenging activity per mole of scavenger. If the scavenger molecule is a polymer in which each repeated unit has scavenging activity then the molar concentration of the repeated unit is the pertinent variable); those that have a free radical scavenging activity at least 20 percent that of Vitamin E are even more preferred; most preferred are those that have a activity at least as great as that of Vitamin E.

As will be evident from the Examples, the fluorimetric process is normally applied substantially simultaneously to a large number of cells.

In one preferred embodiment of the process, step (4) comprises measuring light emitted at wavelengths between about 520 nm and 560 nm (especially at about 520 nm), most preferably where the absorption wavelengths of step (3) are less than 520 nm.

A preferred embodiment of the fluorimetric process further comprises a wash step between the steps numbered (2) and (3). A wash step can be performed by centrifuging the cell out of the solution in which it is suspended, then suspending it in a wash solution, and then centrifuging it out of the wash solution. A wash solution is generally a probe-free solution.

It is preferred that the free radical scavenger not be a fluorescent molecule that emits light at the fluorescent emission wavelength of the probe. In particular, it is preferred that the free radical scavenger neither absorb light at the fluorescent absorption wavelength of the probe nor emit light at the fluorescent emission wavelength of the probe.

In a particular embodiment of the process, the solution that is used in step (2) comprises a fluorescent probe, a free radical scavenger and a fixative. Such a probe solution is itself an invention.

A fluorescent probe that binds to a target molecule is preferably one which binds to that target with high specificity. Such a probe may be a fluorescent dye unattached to a nucleic acid or antibody or other molecule. More preferably, a fluorescent probe is a fluorescent dye covalently attached to a nucleic acid molecule, antibody or other molecule capable of binding specifically to a target molecule. The fluorescent dye may be covalently attached directly to the molecule having target specificity or it may be covalently attached to a linker group which in turn is covalently attached to the molecule having target specificity. The probe nucleic acid molecule will be specific for a nucleic acid target molecule with a base sequence complementary to the probe nucleic acid molecule. The probe antibody will be specific for a target antigen.

Nucleic acid probes can be used against a variety of nucleic acid targets, viral, prokaryotic, and eukaryotic. The target may be a DNA target such as a gene (e.g., oncogene), control element (e.g., promoter, repressor, or enhancer), or sequence coding for ribosomal RNA, transfer RNA, or RNase P. The target may be RNA such as mRNA, ribosomal RNA, RNase P, tRNA, a viral genome or complementary copy thereof. Additionally, the target may be a "nucleic acid amplification product," i.e., a nucleic acid molecule, either DNA or RNA, which is the result of introducing an enzyme or enzymes into the cell so that such enzymes will make an nucleic acid molecule complementary to one already present in the cell. For example, O. Bagasra et al, *The New England Journal of Medicine*, 326, pp. 1385–1391 (1992), have disclosed the use of the polymerase chain reaction (PCR) with intact cells such that the introduction of polymerase molecules into a cell resulted in additional nucleic acid molecules being formed, each a copy of one previously existing in the cell, though not necessarily existing before the introduction of the enzymes.

A viral nucleic acid can be part of a virus, in which case the virus may or may not be inside a cell. Alternatively, a viral nucleic acid target may or may not be part of a virus, but may be inside a cell.

Many publications show how to attach a fluorescent dye to a nucleic acid probe or antibody probe.

The cells containing the target molecules may be eukaryotic cells (e.g., human cells), prokaryotic cells (e.g., bacteria), plant cells, or any other type of cell. They can be simple eukaryotes such as yeast or be derived from the more complex eukaryotes such as humans.

The target molecules can be in a non-enveloped virus or an enveloped virus (having an enveloping membrane such as a lipid-protein membrane).

The hybridization assay may be done with fixed cells or (or fixed viruses). Useful precipitation fixatives include ethanol, acetic acid, methanol, acetone, and combinations thereof. Other useful fixatives will be obvious to one skilled in the art. Fixatives and hybridization of fixed cells, in general, are discussed in PCT international applications, WO 90/02173 and WO 90/02204 of Research Development Corp. Fixatives should provide good preservation of cellular morphology and preservation and accessibility of antigens, and high hybridization efficiency.

The fixative may contain a compound which fixes the cellular components by cross-linking these materials together, for example, paraformaldehyde, glutaraldehyde or formaldehyde. Cross-linking agents, while preserving ultrastructure, often reduce hybridization efficiency; they form networks trapping nucleic acids and antigens and rendering them inaccessible to probes and antibodies. Some also covalently modify nucleic acids preventing later hybrid formation.

The hybridization solution may typically comprise a chaotropic denaturing agent, a buffer, a pore forming agent, a hybrid stabilizing agent.

The chaotropic denaturing agents (Robinson, D. W. and Grant, M. E. (1966) J. Biol. Chem. 241: 4030; Hamaguchi, K. and Geiduscheck, E. P. (1962) J. Am. Chem. Soc. 84: 1329) include formamide, urea, thiocyanate, guanidine, trichloroacetate, tetramethylamine, perchlorate, and sodium iodide. Any buffer which maintains pH at least between 7.0 and 8.0 may be utilized.

The pore forming agent is for instance, a detergent such as Brij 35, Brij 58, sodium dodecyl sulfate, CHAPS™ Triton X-100. Depending on the location of the target biopolymer, the pore-forming agent is chosen to facilitate probe entry through plasma, or nuclear membranes or cellular compartmental structures. For instance, 0.05% Brij 35 or 0.1% Triton X-100 will permit probe entry through the plasma membrane but not the nuclear membrane. Alternatively, sodium desoxycholate will allow probes to traverse the nuclear membrane. Thus, in order to restrict hybridization to the cytoplasmic biopolymer targets, nuclear membrane pore-forming agents are avoided. Such selective subcellular localization contributes to the specificity and sensitivity of the assay by eliminating probe hybridization to complementary nuclear sequences when the target biopolymer is located in the cytoplasm. Agents other than detergents such as fixatives may serve this function.

Hybrid stabilizing agents such as salts of mono- and di-valent cations are included in the hybridization solution to promote formation of hydrogen bonds between complementary sequences of the probe and its target biopolymer. Preferably sodium chloride at a concentration from 0.15M to 1M is used. In order to prevent non-specific binding of nucleic acid probes, nucleic acids unrelated to the target biopolymers are added to the hybridization solution.

Many types of solid supports may be utilized to practice the invention. Supports which may be utilized include, but are not limited to, glass, Scotch tape (3M), nylon, Gene Screen Plus (New England Nuclear) and nitrocellulose. Most preferably glass microscope slides are used. The use of these supports and the procedures for depositing specimens thereon will be obvious to those of skill in the art. The choice of support material will depend upon the procedure for visualization of cells or viruses and the quantitation procedure used. Some filter materials are not uniformly thick and, thus, shrinking and swelling during in situ hybridization procedures is not uniform. In addition, some supports which autofluoresce will interfere with the determination of low level fluorescence. Glass microscope slides are most preferable as a solid support since they have high signal-to-noise ratios and can be treated to better retain tissue.

In one embodiment of the process, the target biological entity is immobilized on a solid surface (especially a glass slide where the entity is a cell) during steps (1) through (4). In another embodiment, the target cell or virus is suspended in liquid during the entire process and not immobilized on a solid surface.

In another aspect, the invention is a kit which comprises a fluorescent probe and a free radical scavenger. The kit may be configured in a variety of ways. For example, the fluorescent probe and the free radical scavenger may (1) be present in the same solution, or (2) be present in separate solutions; alternatively, either the probe or the scavenger or both of them may be present in solid form, so that they must be dissolved in a solvent or solution prior to use.
Abbreviations

| Compound | Abbreviation |
| --- | --- |
| vitamin E ($\alpha$-tocopherol) | Vit. E. |
| 2,2-diphenyl-1-picrylhydrazyl hydrate | 2,2,DIPH |
| 2,2,6,6-tetramethylpiperidine-N-oxyl | Tempo |
| fluorescein isothiocyanate | FITC |
| ethylene diamine tetraacetic acid | EDTA |
| dimethyl sulfoxide | DMSO |
| dithiothreitol | DTT |
| polyvinylpyrrolidone | PVP |
| polyethylene glycol (circa 4000 Mol. Wt.) | PEG 4000 |

Targets in cells, tissue, and fluids

The hybridization assay can be done for targets in cells in liquid suspension, in cells on slides or other solid supports, and in tissue sections. Such hybridization procedures are well known in the art. They are, for example, described in more detail in PCT applications WO 90/02173 and WO 90/02204.

The target molecules can be in eukaryotic cells or prokaryotic cells. The cells can come from solid tissue (e.g., nerves, muscle, heart, skin, lungs, kidneys, pancreas, spleen, lymph nodes, testes, cervix, and brain) or cells present in membranes lining various tracts, conduits and cavities (such as the gastrointestinal tract, urinary tract, vas deferens, uterine cavity, uterine tube, vagina, respiratory tract, nasal cavity, oral cavity, pharynx, larynx, trachea, bronchi and lungs) or cells in an organism's fluids (e.g., urine, stomach fluid, sputum, blood and lymph fluid) or stool.

Flow cytometry

A Coulter Profile II flow cytometer was used. (A typical useful PMT settings are a PMT 1 setting of 1100 and a PMT 3 setting of 900, with color compensation, PMT 1–PMT 3, of 15%).

For experiments with FITC as the probe dye, the dye was first excited with light of 488 nm and then the emitted light was measured. For the emitted light (for LFL1), a 540 bp (40) filter was used; i.e., only light with a wavelength between 520 nm and 560 nm is allowed to pass. The filter for LFL3 was a 635 long pass filter; i.e., it allows any light over 635 nm wavelength to pass.

Solutions used in the Examples

The following solutions were those used in the Examples.

Fixation solution F had the following ingredients: 4 volumes ethanol, 5 volumes of 1×PBS, 1 volume of glacial acetic acid.

Hybridization cocktail HC had the following ingredients; 5×SSC (0.75M NaCl, 0.075M sodium citrate); 30% Formamide (v/v); 3% Triton X-100 (v/v); 0.4M Guanidinium isothiocyanate; 0.16M sodium phosphate buffer (pH 6); 15×Ficoll/PVP (polysucrose 400,000 mol wt/polyvinylpyrrolidone); 1 mg/ml Sheared Salmon Sperm DNA; 10 mM EDTA; 25 mM DTT; 5% PEG 4000. In the foregoing, 500×Ficoll/PVP is 5 g of Ficoll type 400 (polysucrose 400.00 mol wt) plus 5 g of PVP (polyvinylpyrrolidone) dissolved in water to a total volume of 100 ml; 15×Ficoll/PVP indicates that 500×Ficoll/PVP has been diluted by a factor of 15/500 with water.

Ficoll (Pharmacia) is a nonionic synthetic polymer of sucrose.

If a free radical scavenger is added to the cocktail, its preferred concentration is from 0.1% to 10% (v/v).

For hybridization cocktails used with a nucleic acid probe, the temperature for the hybridization reaction preferably between 30° C. and 46° C.; the time preferably is between 5 minutes and 16 hours.

Wash solution #1 had the following composition: 0.4M guanidinium isothiocyanate; 0.1% Triton X-100 (an alcohol derivative of polyoxyethylene ether, see Aldrich Chemical Co. catalogue for 1990–91; 0.1% v/v); 0.1×SSC; in deionized water.

Wash solution #2 had the following composition: 0.1% Triton X-100 (v/v); 0.1×SSC; in deionized water.

1×SSC had the following composition: 0.15M NaCl, 0.015M sodium citrate, pH 7.0. 2×SSC was composed so that upon a 1:1 dilution with water, SSC would be produced; 10×SSC was composed so that upon a 1:10 dilution with water, SSC would be produced.

1×PBS was phosphate-buffered saline and had the formula, 0.136M NaCl, 0.003M KCl, 0.008M Na$_2$HPO$_4$·7H$_2$O, 0.001M KH$_2$PO$_4$.

If a dye-labeled antibody is used as the probe, then the probe may be dissolved in PBS, possibly supplemented with bovine serum albumin (BSA) while it is allowed to react with target cells preferably at a temperature in the range 4° C. to 34° C. The cells need not be fixed (e.g. when the antibody target is a cell-surface antigen), or may be fixed after the probe-target incubation is completed, or may be fixed prior or during the probe-target incubation. The free radical scavenger is preferably present while the probe is being mixed with the target cells.

Additional useful reagents and solutions

Useful reagents and solutions for executing the inventions described herein include 0.0025% Evans Blue and/or 10% dodecyl alcohol in the solution analyzed cytofluorimetrically; about 8% DMSO (v/v) with about 5% or 10% squalane and about 5% or 10% pyrrolidinone in the hybridization cocktail when the target is in a biological entity; 5 µl of 1M (1 molar) DTT and 5 µl of Proteinase K (1 mg/ml) solution are added to 100 µl of cocktail and the hybridization reactin is run, for example, at 42° C. for 5 min, then at 95° C. for 5 min, and then at 42° C. for 2 min, when the target is in a biological entity; and/or about 0.05% or 0.10% aurintricarboxylic acid in the hybridization cocktail when the target is a biological entity and a fluorescent probe, especially one with a fluoresein or rhodamine derivative as a reporter group, is used.

Probes, where the target is in a biological entity can be made as phosphorothioate oligonucleotides, each 30-mer having four sulfur atoms, using an Applied Biosystem (ABI) DNA Synthesizer, Model 380B and the recommended ABI reagents. The sulfur atoms may be located as follows: one is at the extreme 5' end of the probe, a second is between the 7th and 8th nucleosides (counting from the 5' end), the third is between the 22nd and 23rd nucleosides, and the fourth is between the 29th and 30th nucleosides. The sulfur atoms of the polysulfurized oligonucleotides can then coupled to a fluorescent dye, iodoacetamido-fluorescein, as follows (smaller amounts can be synthesized by adjusting the volumes): 200 µg of dried oligonucleotide is dissolved in 100 µl of 250 mM Tris buffer, pH 7.4 to form a first solution. Then one mg of iodoacetamido-fluorescein is combined with 100 µl of dry dimethylformamide (i.e., 100 percent DMF) in a second solution. The two solutions are mixed together and shaken overnight. After the overnight incubation, the labeled oligonucleotide is precipitated with ethanol and 3M sodium acetate. This crude material is then loaded on to a PD-10 column to remove free dye. The desired fractions are then collected. The liquid phase is then removed under vacuum. The crude material is then purified with HPLC (high performance liquid chromatography).

Where 30-mers are used, probes against both strands of a double-stranded target can be used, provided that the probes are "out-of phase" along the map of the target so that any probe is not complementary in base sequence to more than about 15 nucleotides of a probe to the other strand of the target. In that way, probes hybridize to the target and not to each other.

Cell lines used in the Examples

ALEX cells are a human cell line.

Probes

The NR probe was a fluorescein-labeled DNA oligomer specific for the bacterial nitrogen reductase gene. It had the nucleotide sequence ATCAGAGTAGTGGTATTTCAC-CGGC (SEQ ID NO: 1). (For all sequences, described herein, the 5' end is at the left end.)

The 28S RNA probe was a fluorescein labeled DNA oligomer specific for a human 28S RNA nucleotide sequence. It had the sequence TACGCTCGATCCAGCTAT-CAGCCGT (SEQ ID NO: 2).

Both the NR and 28S probes were oligodeoxyribonucleotides synthesized on an Applied Biosystems (A.B.I.) DNA synthesizer Model 380 using the recommended A.B.I. reagents. In the last stage of the synthesis, an aminohexyl linker was attached to the 5' end phosphate. The 5' aminohexyl oligodeoxyribonucleotides were then coupled to a FITC dye molecule from Molecular Probes and purified by HPLC.

Reagents

Reagents can be purchased from any of a variety of sources including Aldrich Chemical Co., Milwaukee, Wis., Sigma Chemical Co., St. Louis, Mo., Molecular Probes, Inc., Eugene, Oreg., Clontech, Palo Alto, Calif., Kodak, Rochester, N.Y., and SPectrum Chemical Manufacturing Corp., Gardenea, Calif.

EXAMPLES

EXAMPLE 1

Ability of Free Radical Enhancers to Decrease Autofluorescence

In this Example, the assay cocktail was a hybridization cocktail, one that is useful when the target-specific moiety of the probe is a nucleic acid and the target is a nucleic acid. The experiments were conducted as follows:

1. ALEX cells were fixed in solution F, then resuspended in 2×SSC.
2. The cells were spun out of solution and resuspended in hybridization cocktail HC. The HC cocktail varied from sample to sample only as regards to the free radical scavenger present (if any was added at all).
3. After 30 min. at 42° C., the cells were washed in wash solution #1 preheated to 42° C. by centrifuging out of the hybridization cocktail at 250×g for 5 minutes.
4. Cells were next washed in wash solution #2 preheated to 42° C.
5. Cells were resuspended in a 1×PBS solution.
6. Cells were run on a flow cytometer and histograms were generated which displayed the autofluorescence on one axis (LFL3) and the probe fluorescence on the other axis (LFL1).

In step (6) a "Count vs. LFL1" histogram was generated. ("Count" refers to cell count.) This histogram was used as the basis for determining whether the compound tested was an effective autofluorescence reducer. Additional histograms and an FS/SS plot were also generated but were not used as the basis for determining autofluorescence reduction; they are not shown or summarized here.

An example of a Count vs. LFL1 histogram that was generated using no free radical scavenger is shown in FIG. 1. The number of cells counted was 3471. The minimum and maximum LFL1 settings were 0.102 and 1023, respectively.

Figure 2:
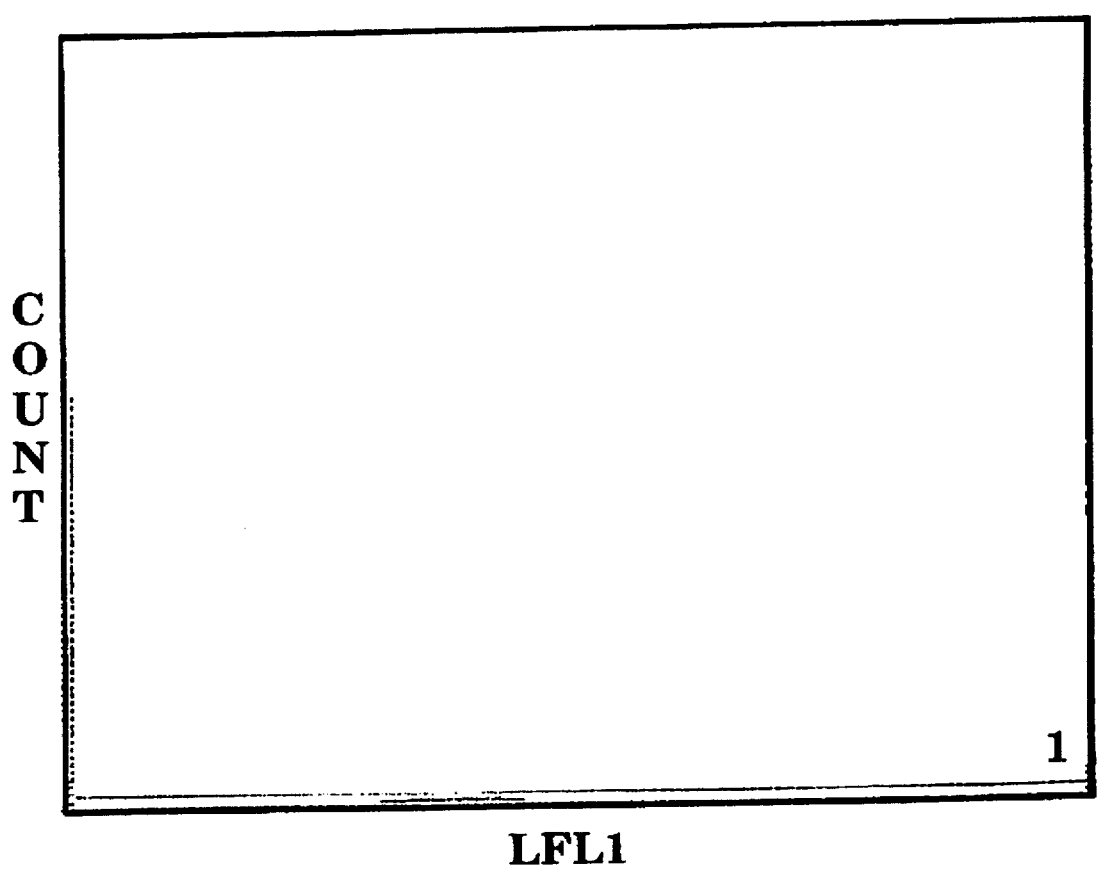

An example of such a histogram generated using vitamin E as a free radical scavenger is shown in FIG. 2. The number of cells counted was 6432. The minimum and maximum LFL1 settings were 0.102 and 1023, respectively.

TABLE 1

Mean LFL1 & LFL3 using free radical scavengers

| Added Compound | Mean LFL1 | Mean LFL3 |
| --- | --- | --- |
| none | 7.92 | 0.22 |
| vit. E | 0.501 | 0.119 |
| 2,2,DIPH | 17.27 | 0.863 |
| Tempo | 3.23 | 0.181 |
| Thiophenol | 1.69 | 0.138 |

In Table 1, "Added Compound" is the compound added (at 5% v/v for liquids such as Vitamin E, at 5 g/100 ml for solids) to the assay cocktail.

An indicator of auto fluorescence reduction due to a free radical scavenger is the difference between the mean LFL1 intensity using just cocktail and the mean LFL1 intensity using cocktail plus a free-radical scavenger. Another indicator is the difference between the mean LFL3 intensity using just cocktail and the mean LFL3 intensity using cocktail plus a free radical scavenger. The results show that Tempo, thiophenol, and vitamin E are free radical scavengers that are effective autofluorescence reducers for the combination of fluorescent absorption emission wavelengths utilized in this Example. On the other hand, the results show that 2,2,DIPH can not be an used as an auto fluorescence reducer under those conditions. The ineffectiveness of 2,2, DIPH was probably not due to the fact that it did not reduce the autofluorescence, but rather to the fact that it is a fluorescent compound that emits light at the wavelengths monitored in this Example. A similar problem was observed with the free radical scavenger, Vitamin K.

EXAMPLE 2

Use of Vitamin E in Assay Specific for 28S RNA

The procedure of Example 1 was followed except that uninfected H9 cells were used instead of ALEX cells, and either the NR probe or the 28S RNA probe was present in the HC cocktail at a concentration of 10 ug/ml (microgram/ml). The NR probe was specific for a bacterial nitrogen reductase gene not present in human cells. It was used as a negative control.

The 28S RNA probe was specific for a human 28S RNA sequence.

The results are shown in Table 2.

TABLE 2

| Probe | Vitamin E in HC cocktail? | LFL1 |
| --- | --- | --- |
| NR | No | 13.27 |
| NR | Yes | 8.86 |
| 28S | No | 251 |
| 28S | Yes | 231 |

The results showed that the presence of Vitamin E in the hybridization cocktail resulted in an approximately 33 percent decrease in the undesirable background level (NR results) but only an 8 percent decrease in the signal level seen with the target specific probe of interest (28S RNA).

Having thus described the invention, what is desired to protect by Letters Patent and hereby claim is:

1. An in situ fluorimetric process which process comprises the steps of:
   (a) contacting a biological entity with a solution comprising a fluorescent probe that binds to a target molecule in or on said biological entity, said contacting performed in a manner such that said fluorescent probe binds to said target molecule so as to make said fluorescent probe a biological entity-bound probe,
   (b) contacting the biological entity with a solution comprising a free radical scavenger selected from the group consisting of Vitamin E, thiophenol and 2,2,6,6,-tetramethyl-piperidine-N-oxyl for a period of time of not less than 5 minutes and not more than 16 hours,
   (c) causing the biological entity-bound probe to absorb light of wavelengths that are fluorescent absorption wavelengths of said biological entity-bound probe, and
   (d) detecting light of a wavelengths that are fluorescent emission wavelengths of said biological entity-bound probe;
   wherein step (a) takes place before step (b), after step (b),or during step (b),
   wherein said biological entity is a cell or a virus, and
   wherein the autofluorescence that contributes to the light detected during step (d) is less in the presence of said free radical scavenger than in the absence of said free radical scavenger.

2. The process of claim 1, wherein said fluorescent probe comprises either a nucleic acid moiety or an antibody moiety.

3. The process of claim 1, wherein steps (a) and (b) are performed simultaneously by incorporating said fluorescent probe and said free radical scavenger in one solution.

4. The process of claim 1, wherein step (d) comprises measuring light emitted between about 520 nm and 560 nm.

5. The process of claim 4, wherein said fluorescent probe has a fluorescein moiety.

6. The process of claim 1, said process further comprising a wash step between said steps (b) and (c), said wash step comprising washing said biological entity in a solution that is free of fluorescent probe.

7. The process of claim 6, wherein said fluorescent probe comprises either a nucleic acid moiety or an antibody moiety.

8. The process of claim 6, wherein steps (a) and (b) are performed simultaneously by incorporating said fluorescent probe and said free radical scavenger in one solution.

9. The process of claim 6, wherein said biological entity is a cell.

10. The process of claim 6, wherein said fluorescent probe is a fluorescent dye covalently linked to a nucleic acid moiety.

11. The process of claim 1, wherein said biological entity is treated with a fixative prior to step (a).

12. The process of claim 11, wherein said fluorescent probe comprises either a nucleic acid moiety or an antibody moiety.

13. The process of claim 11, wherein steps (a) and (b) are performed simultaneously by incorporating said fluorescent probe and said free radical scavenger in one solution.

14. The process of claim 11, wherein said biological entity is a cell.

15. The process of claim 11, wherein said fluorescent probe is a fluorescent dye covalently linked to a nucleic acid.

16. The process of claim 1, wherein said fluorescent probe is a fluorescent dye covalently linked to a nucleic acid moiety to form a nucleic acid probe.

17. The process of claim 16, wherein said nucleic acid probe is complementary to a specific DNA sequence in said biological entity.

18. The process of claim 16, wherein said nucleic acid probe is complementary to a specific RNA sequence in said biological entity.

19. The process of claim 16, wherein said target molecule is viral DNA.

20. The process of claim 16, wherein said target molecule is viral RNA.

21. The process of claim 16, wherein said target molecule is human immunodeficiency virus RNA or DNA.

22. The process of claim 1, wherein said biological entity is suspended in liquid.

23. The process of claim 1, wherein said biological entity is immobilized on a solid support.

24. The process of claim 23, wherein said biological entity is present in a tissue section.

25. The process of claim 23, wherein said biological entity is not a tissue section.

26. The process of claim 1 wherein said biological entity is a cell.

27. The process of claim 26, wherein said cell is a eukaryotic cell.

28. The process of claim 27, wherein said eukaryotic cell is a human cell.

29. The process of claim 28, wherein said fluorescent probe is complementary for a viral nucleic acid.

30. The process of claim 29, wherein said target molecule is human immunodeficiency virus RNA or DNA.

31. The process of claim 26, wherein said cell is a prokaryotic cell.

32. The process of claim 26, wherein said cell is a plant cell.

33. The process of claim 1, wherein said biological entity is a virus.

34. The process of claim 33, wherein said target molecule is human immunodeficiency virus RNA or DNA.

35. The process of claim 1, where said fluorescent probe is an antibody probe.

36. The process of claim 1, wherein said free radical scavenger is present in solution at a concentration between 0.1% and 10% (v/v).

37. The process of claim 36, wherein said fluorescent probe comprises either a nucleic acid moiety or an antibody moiety.

38. The process of claim 36, wherein steps (a) and (b) are performed simultaneously by incorporating said fluorescent probe and said free radical scavenger in one solution.

39. The process of claim 36, wherein said biological entity is a cell.

40. The process of claim 36, wherein said fluorescent probe is a fluorescent dye covalently linked to a nucleic acid moiety.

* * * * *